(12) United States Patent
Martin et al.

(10) Patent No.: US 12,191,003 B2
(45) Date of Patent: Jan. 7, 2025

(54) REAL-TIME PREDICTION OF CHEMICAL PROPERTIES THROUGH COMBINING CALCULATED, STRUCTURED AND UNSTRUCTURED DATA AT LARGE SCALE

(71) Applicant: International Business Machines Corporation, Armonk, NY (US)

(72) Inventors: Richard L. Martin, Jamaica Plain, MA (US); Sheng Hua Bao, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 1740 days.

(21) Appl. No.: 16/148,159

(22) Filed: Oct. 1, 2018

(65) Prior Publication Data

US 2020/0104465 A1    Apr. 2, 2020

(51) Int. Cl.
*G01N 33/48* (2006.01)
*G01N 33/50* (2006.01)
(Continued)

(52) U.S. Cl.
CPC ............. *G16C 20/30* (2019.02); *G16C 20/70* (2019.02)

(58) Field of Classification Search
CPC ................................ G16C 20/30; G16C 20/70
See application file for complete search history.

(56) References Cited

U.S. PATENT DOCUMENTS 6,651,008 B1    11/2003   Vaisberg et al.
6,898,533 B1    5/2005    Miller et al.
(Continued)

FOREIGN PATENT DOCUMENTS

KR        101375672 B2    3/2014

OTHER PUBLICATIONS

Anis et al. A pattern recognition approach for prediction of protein drug interactions using neural networks. Journal of American Science, vol. 9, pp. 51-56. (Year: 2013).*
(Continued)

*Primary Examiner* — Russell S Negin
(74) *Attorney, Agent, or Firm* — Stephen J. Walder, Jr.; Jordan Schiller

(57) ABSTRACT

A mechanism is provided in a data processing system comprising at least one processor and a memory comprising instructions which, when executed by the at least one processor, causes the at least one processor to implement a real-time prediction engine for real-time predication of chemical properties through combining calculated, structured, and unstructured data at large scale. Offline components executing within the real-time prediction engine store a computational representation for each of a plurality of chemical structures in a unified storage. Each computational representation maps a respective chemical structure to a vector of calculated chemical structure features and properties, unstructured chemical features and properties, and structured chemical features and properties. The offline components train a computational real-time predictive model based on the computational representations. A user interface executing within the real-time prediction engine receives a request specifying one or more chemical compounds. An analytics jobs manager executing within the real-time prediction engine predicts one or more properties of the one or more chemical compounds using the computational real-time predictive model. The analytics jobs manager outputs the one or more properties of the one or more chemical compounds to the user interface.

20 Claims, 5 Drawing Sheets

(51) Int. Cl.
*G16C 20/30* (2019.01)
*G16C 20/70* (2019.01)

(56) References Cited

U.S. PATENT DOCUMENTS

| | | |
|---|---|---|
| 6,996,473 B2 | 2/2006 | Grass et al. |
| 7,856,321 B2 | 12/2010 | Lanza et al. |
| 8,473,448 B2 | 6/2013 | Yuta |
| 8,949,157 B2 | 2/2015 | Okuno et al. |
| 2003/0115030 A1* | 6/2003 | Ewing .................. G16C 20/30 703/11 |
| 2003/0177143 A1 | 9/2003 | Gardner |
| 2004/0093331 A1 | 5/2004 | Garner et al. |
| 2010/0332287 A1 | 12/2010 | Gates et al. |
| 2012/0323558 A1 | 12/2012 | Nolan et al. |

OTHER PUBLICATIONS

Jain et al. 2020 International Conference in Emerging Smart Computing and Informatics, pp. 164-169. (Year: 2020).*

Bernazzani, Luca et al., "Predicting Physical-Chemical Properties of Compounds from Molecular Structures by Recursive Neural Networks", Journal of Chemical Information and Modeling, Sep. 2006 46 (5), 13 pages.

Schutt, K.T. et al., "SchNet: A continuous-filter convolutional neural network for modeling quantum interactions", https://arxiv.org/pdf/1706.08566.pdf, arXiv: 1706.08566v5 [stat.ML] Dec. 19, 2017, 11 pages.

* cited by examiner

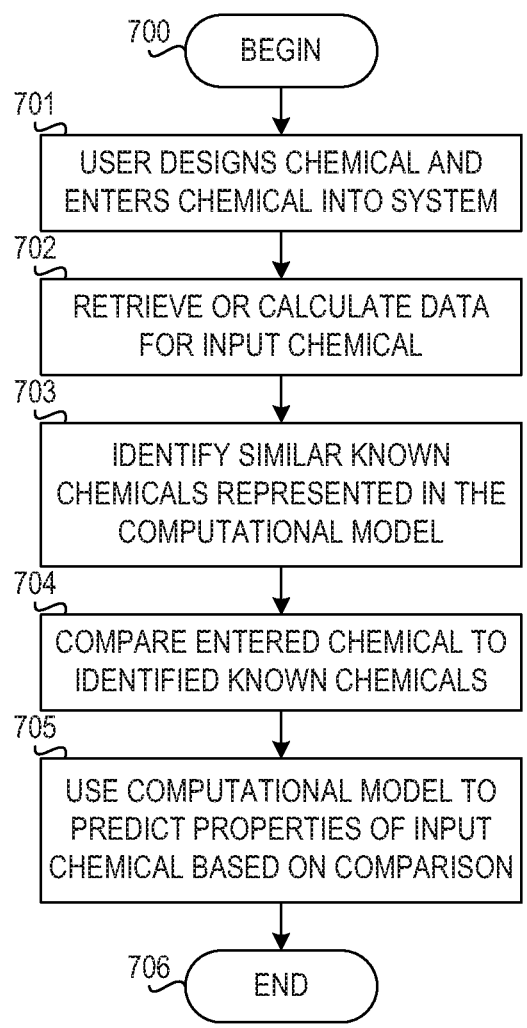

REAL-TIME PREDICTION OF CHEMICAL PROPERTIES THROUGH COMBINING CALCULATED, STRUCTURED AND UNSTRUCTURED DATA AT LARGE SCALE

BACKGROUND

The present application relates generally to an improved data processing apparatus and method and more specifically to mechanisms for real-time prediction of chemical properties through combining calculated, structured and unstructured data at large scale.

The creation of new chemical products is of fundamental business importance to multiple industries, including but not limited to pharmaceuticals, agrochemicals, biotechnology, and related areas. The scope of chemical products includes but is not limited to individual chemical compounds and combinations of chemical compounds, which include both active and inactive ingredients. Identifying chemicals with optimal or near-optimal properties for a particular application is a critical step in the creation of new chemical products and is also one of the most challenging research tasks in these industries.

Due to the essentially unlimited space of possible chemical compounds, exhaustive experimental testing is infeasible. Consequently, computational approaches to predicting chemical properties are the subject of much research and include approaches involving simulation, informatics, and data science techniques. However, reliable computational predictions remain elusive, in part because these techniques can consider only a small number of the many factors that imbue a chemical with a particular property or set of properties required for a given application; for example, computational drug discovery requires prediction of multiple properties of chemicals, including solubility and excretion, as well as the desired potency and indeed any off-target potencies that are often the cause of drug side effects. Furthermore, computational predictions, particularly those that involve performing simulations, are often very time consuming and require expert configuration, such as selecting force field parameters.

The ability to reliably predict chemical properties in real-time would revolutionize drug discovery and many other industries that rely on the creation of new chemical products. Due to recent advances in unstructured data processing, such as natural language processing and image processing, it is now possible to conceive of a system and method that utilizes unstructured data in addition to structured and calculated data, at very large scales (e.g., tens of millions of documents) to make such predictions in real time.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and a memory comprising instructions which, when executed by the at least one processor, causes the at least one processor to implement a real-time prediction engine for real-time predication of chemical properties through combining calculated, structured, and unstructured data at large scale. The method comprises storing, by offline components executing within the real-time prediction engine, a computational representation for each of a plurality of chemical structures in a unified storage. Each computational representation maps a respective chemical structure to a vector of calculated chemical structure features and properties, unstructured chemical features and properties, and structured chemical features and properties. The method further comprises training, by the offline components, a computational real-time predictive model based on the computational representations. The method further comprises receiving, by a user interface executing within the real-time prediction engine, a request specifying one or more chemical compounds. The method further comprises predicting, by an analytics jobs manager executing within the real-time prediction engine, one or more properties of the one or more chemical compounds using the computational real-time predictive model. The method further comprises outputting, by the analytics jobs manager, the one or more properties of the one or more chemical compounds to the user interface. The illustrative embodiment allows prediction of chemical properties in real-time for a chemical that has not been produced based on known properties of known chemicals.

In one example embodiment, the method further comprises processing, by the offline components, unstructured data describing the plurality of chemical structures to extract unstructured chemical features and properties.

In another example embodiment, the unstructured chemical features and properties comprise generic names, systematic names, adjacent or co-occurring words or phrases, relationships between the chemical structure and words or phrases, assertion of attributes, or assertion of effects of the chemical structure.

In another example embodiment, the method further comprises processing, by the offline components, structured data describing the plurality of chemicals to extract structured chemical features and properties.

In yet another example embodiment, the structured chemical features and properties comprise molecular weight or $IC_{50}$ values.

In another example embodiment, the method of further comprises generating, by the offline components for each of the plurality of chemicals, chemical structure features based on the unstructured data and the structured data.

In one example embodiment, the chemical structure features comprise an atomistic structure of the chemical structure or a two- or three-dimensional representation, or a two-dimensional chemical graph or connection table describing how individual constituent atoms of the chemical structure are chemically bonded.

In another example embodiment, the computational real-time predictive model comprises a machine learning model, a deep learning model, or a neural network.

In yet another example embodiment, predicting the one or more properties of the one or more chemical compounds comprises sending by an analytics job server a plurality of real-time predictive analytics jobs to a plurality of analytics job worker components.

In another example embodiment, predicting the one or more properties of the one or more chemical compounds comprises identifying chemical structures similar to the one or more chemical compounds; comparing the one or more chemical compounds to the identified similar chemical structures; and using the computational real-time predictive model to predict the one or more properties of the one or more chemical compounds based on results of the comparison.

In another illustrative embodiment, a computer program product comprises a computer readable storage medium having a computer readable program stored therein. The computer readable program, when executed on a computing device, causes the computing device to implement a real-time prediction engine for real-time predication of chemical properties through combining calculated, structured, and unstructured data at large scale. The computer readable program causes the computing device to store, by offline components executing within the real-time prediction engine, a computational representation for each of a plurality of chemical structures in a unified storage. Each computational representation maps a respective chemical structure to a vector of calculated chemical structure features and properties, unstructured chemical features and properties, and structured chemical features and properties. The computer readable program further cause the computing device to train, by the offline components, a computational real-time predictive model based on the computational representations. The computer readable program further cause the computing device to receive, by a user interface executing within the real-time prediction engine, a request specifying one or more chemical compounds. The computer readable program further cause the computing device to predict, by an analytics jobs manager executing within the real-time prediction engine, one or more properties of the one or more chemical compounds using the computational real-time predictive model. The computer readable program further cause the computing device to output, by the analytics jobs manager, the one or more properties of the one or more chemical compounds to the user interface. The illustrative embodiment allows prediction of chemical properties in real-time for a chemical that has not been produced based on known properties of known chemicals.

In one example embodiment, the computer readable program causes the computing device to process, by the offline components, unstructured data describing the plurality of chemical structures to extract unstructured chemical features and properties.

In another example embodiment, the unstructured chemical features and properties comprise generic names, systematic names, adjacent or co-occurring words or phrases, relationships between the chemical structure and words or phrases, assertion of attributes, or assertion of effects of the chemical structure.

In another example embodiment, the computer readable program causes the computing device to process, by the offline components, structured data describing the plurality of chemicals to extract structured chemical features and properties.

In yet another example embodiment, the structured chemical features and properties comprise molecular weight or $IC_{50}$ values.

In another example embodiment, the computer readable program causes the computing device to generate, by the offline components for each of the plurality of chemicals, chemical structure features based on the unstructured data and the structured data.

In one example embodiment, the chemical structure features comprise an atomistic structure of the chemical structure or a two- or three-dimensional representation, or a two-dimensional chemical graph or connection table describing how individual constituent atoms of the chemical structure are chemically bonded.

In another example embodiment, the computational real-time predictive model comprises a machine learning model, a deep learning model, or a neural network.

In yet another example embodiment, predicting the one or more properties of the one or more chemical compounds comprises sending by an analytics job server a plurality of real-time predictive analytics jobs to a plurality of analytics job worker components.

In another illustrative embodiment, an apparatus comprises a processor and a memory coupled to the processor. The memory comprises instructions which, when executed by the processor, cause the processor to implement a real-time prediction engine for real-time predication of chemical properties through combining calculated, structured, and unstructured data at large scale. The instructions cause the processor to store, by offline components executing within the real-time prediction engine, a computational representation for each of a plurality of chemical structures in a unified storage. Each computational representation maps a respective chemical structure to a vector of calculated chemical structure features and properties, unstructured chemical features and properties, and structured chemical features and properties. The instructions cause the processor to train, by the offline components, a computational real-time predictive model based on the computational representations. The instructions further cause the processor to receive, by a user interface executing within the real-time prediction engine, a request specifying one or more chemical compounds. The instructions further cause the processor to predict, by an analytics jobs manager executing within the real-time prediction engine, one or more properties of the one or more chemical compounds using the computational real-time predictive model. The instructions further cause the processor to output, by the analytics jobs manager, the one or more properties of the one or more chemical compounds to the user interface. The illustrative embodiment allows prediction of chemical properties in real-time for a chemical that has not been produced based on known properties of known chemicals.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 7 is a flowchart illustrating operation of a software engine for large scale data analytics and real-time prediction in accordance with an illustrative embodiment.

DETAILED DESCRIPTION

Figure 1:
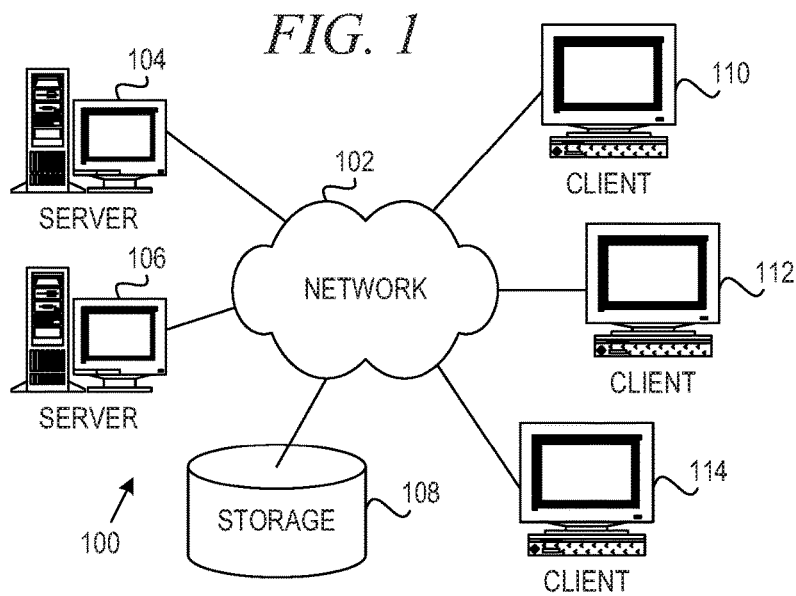
FIG. 1 is an example diagram of a distributed data processing system in which aspects of the illustrative embodiments may be implemented.

The illustrative embodiments concern the combination of large scale structured, unstructured, and calculated data for the real-time prediction of chemical properties. The illustrative embodiments provide a real-time analytics engine that takes as input data extracted from structured and unstructured data sources. The real-time analytics engine produces output that is readable by a human or by software and constitutes one or more predictions of one or more properties of one or more chemicals. The real-time analytics engine may be an independent engine that reads this data from other independent engines that perform the processing of structured and unstructured data sources, or the real-time analytics engine may be part of a larger engine that includes the processing of structured and unstructured data sources.

In one embodiment, the real-time analytics engine comprises components that combine unstructured and structured data with calculated data into a storage system for chemical structures and associated features and properties. In another embodiment, the real-time analytics engine comprises offline components for processing large scale data sources and storing extracted and calculated information. The real-time analytics engine comprises front-end components for receiving requests from a user interface, Representational State Transfer (REST) service calls, etc. The real-time analytics engine also comprises back-end components for processing the real-time requests, retrieving the appropriate data, and submitting jobs to an analytics jobs server, which performs predictions in real time.

In one example embodiment, the analytics jobs server employs analytics jobs workers to perform portions of the analytics processing in parallel. The analytics jobs workers can be extended for scalability.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
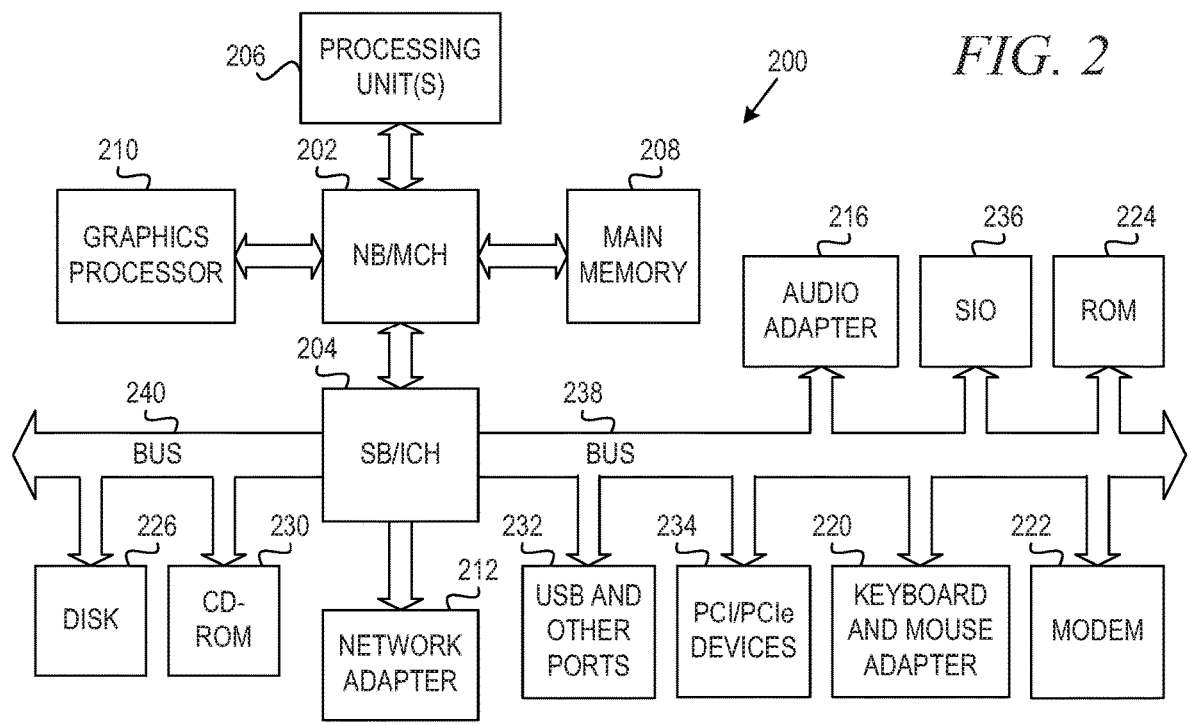
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104, may be specifically configured to implement a real-time analytics engine. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates real-time prediction of chemical properties through combining calculated, structured, and unstructured data at large scale.

As noted above, the mechanisms of the illustrative embodiments utilize specifically configured computing devices, or data processing systems, to perform the operations for real-time analytics. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external effects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System p® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the real-time prediction of chemical properties through combining calculated, structured, and unstructured data.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
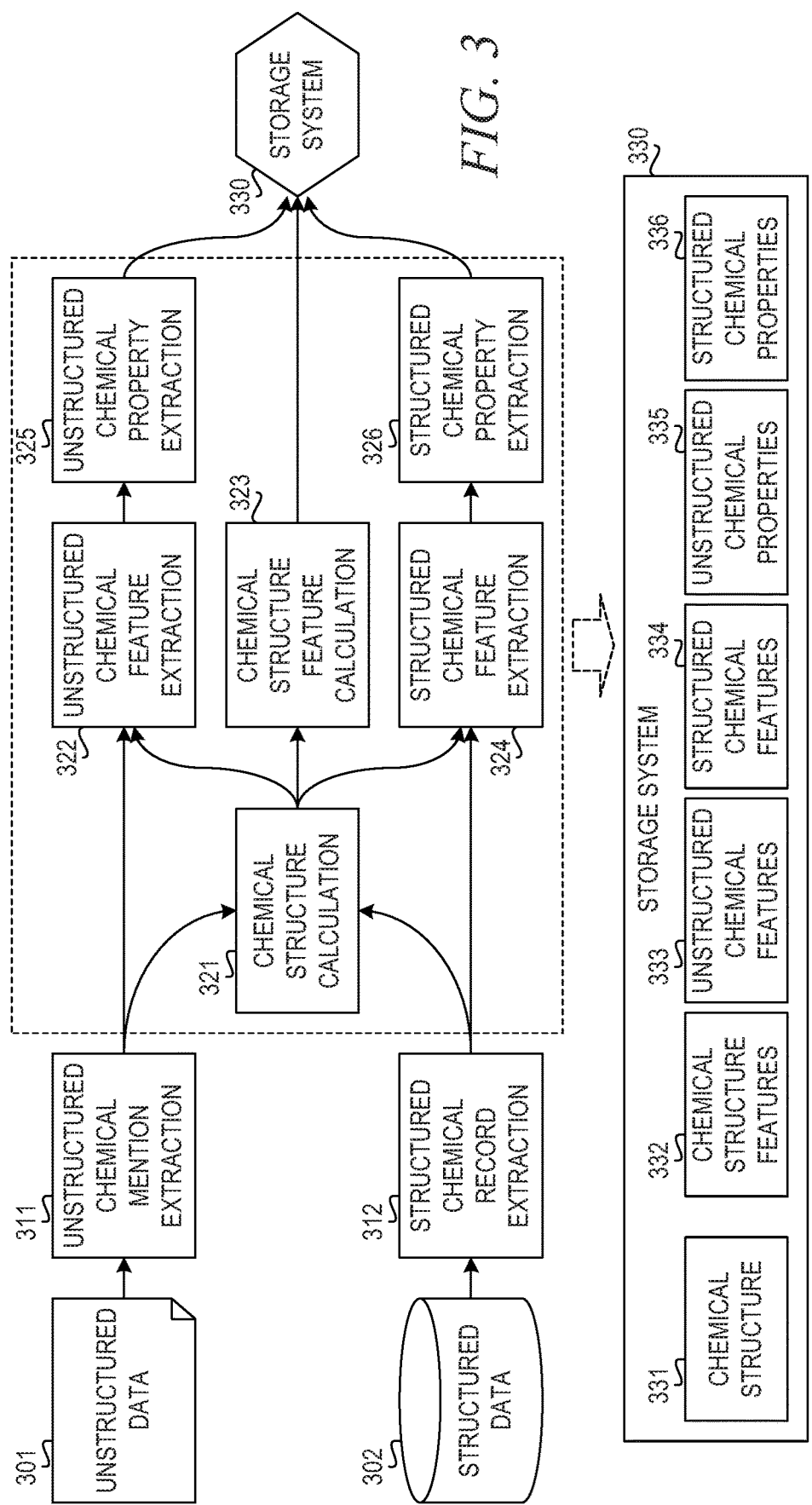
FIG. 3 is a block diagram illustrating various components for generating and storing structured, unstructured, and calculated data in a unified storage system in accordance with an illustrative embodiment.

FIG. 3 is a block diagram illustrating various components for generating and storing structured, unstructured, and calculated data in a unified storage system in accordance with an illustrative embodiment. The source data comprises both unstructured data 301 and unstructured data 302. In one embodiment, unstructured data 301 include, for example, large scale data including tens of millions of documents from the literature, intellectual property documents, etc. In an example embodiment, structured data 302 include, for example, multiple distinct large expert-curated databases. Unstructured chemical mention extraction component 311 extracts chemical mentions from unstructured data 301. Unstructured chemical mention extraction component 311 performs different mention extraction techniques for different unstructured data sources, such as natural language techniques, image processing, etc. Different structured data sources have different schemas to be parsed. Structured chemical record extraction component 312 extracts chemical records from structured data 302.

Chemical structure calculation component 321 calculates the chemical structure of each chemical. The chemical structure is unambiguous and acts as a primary key to map the data extracted from the unstructured and structured sources for that chemical, regardless of whether the specific mention or record of that chemical in those sources was a brand name, generic name, etc. The chemical structure is any representation describing how the atoms of a chemical are bonded, such as a graph or table. Once the chemical structure is calculated, chemical structure feature calculation component 323 calculates features for the chemical structure. In one embodiment, the calculated chemical structure features include specific chemical functional groups (e.g., amine group, carboxylic acid group, etc.), individual smallest ring systems (e.g., five- and six-member rings, etc.), fused ring systems (e.g., naphthalene, etc.), etc.

For each chemical mention or record from unstructured or structured data respectively, unstructured chemical feature extraction component 322 and structured chemical feature extraction component 324 extract features and properties of the chemical from their respective data sources. In one example embodiment, unstructured features include the frequency of occurrence of other words and phrases in the same source text document as the chemical, such as "bag of words" or "word vector" features. In an example embodiment, structured features include basic attributes of a chemical, such as its molecular weight or boiling point.

Unstructured chemical property extraction component 325 extracts chemical properties from the unstructured data and extracted features. In one embodiment, unstructured properties include explicit natural language descriptions of the properties of a chemical, such as "chemical X is known to inhibit the function of protein Y." Structured chemical property extraction component 326 extracts chemical properties from the structured data and extracted features. In an example embodiment, structured properties include specific half maximal inhibitory concentration ($IC_{50}$) values describing the inhibitory strength of the chemical X with respect to the protein Y.

Finally, each chemical structure, along with all the features and properties calculated and extracted for the chemical structure are deposited into a storage system 330, each element of which can be considered as a mapping between the chemical structure and a vector of its features and properties. Storage system 330 stores for a given chemical structure 331 a vector comprising chemical structure features 332, unstructured chemical features 333, structured chemical features 334, unstructured chemical properties 335, and structured chemical properties 336.

Figure 4:
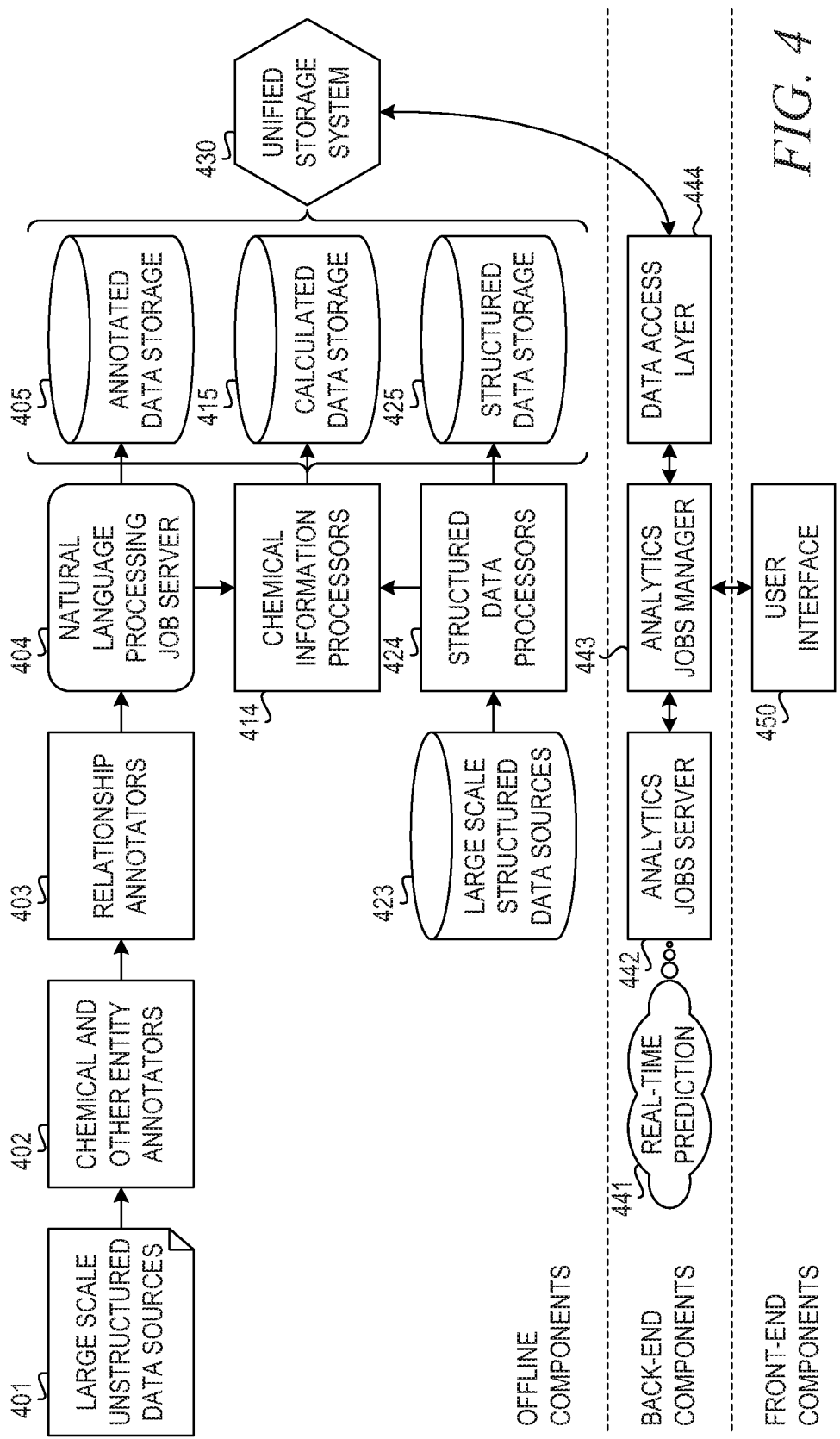
FIG. 4 is a block diagram illustrating components in an extensible computational architecture for large scale data analytics and real-time prediction in accordance with an illustrative embodiment.

FIG. 4 is a block diagram illustrating components in an extensible computational architecture for large scale data analytics and real-time prediction in accordance with an illustrative embodiment. The process of large scale data can take place in an offline workflow, where large scale data is indexed for rapid retrieval. Requests for predictive analytics arrive in real-time from a user interface (UI), Representational State Transfer (REST) service calls, etc. The back-end components process the request, retrieve the appropriate data, and perform the predictive step in real time.

In accordance with the illustrative embodiment, unstructured data from annotated data storage 405 include but are not limited to unstructured data formats that express features or properties of a chemical, including but not limited to natural language text, images, or other media including the context of the mention of the chemical. In an example embodiment, the context of the chemical includes every synonymous text, image or other representation of the chemical, such as generic names and systematic names occurring within a given corpus of unstructured information and the specific encompassing sentence and document, etc., or other encompassing media, including features derived therefrom, including but not limited to adjacent or co-occurring words, phrases, and other entities, which may include those determined to be of a particular entity type, such as genes, proteins, or other chemicals, etc. The unstructured data 405 also include but are not limited to properties of the chemical mention in unstructured data sources, such as natural language text, images or other media. In an example embodiment, the unstructured data 405 include associations and relationships between the chemical or other words or phrases that may or may not be other entity types, including but not limited to the assertion of attributes of the chemical (e.g., an assertion that a chemical has a particular molecular mass or boiling point) and the assertion of effects of the chemical (e.g., an assertion that a chemical affects a particular organism or other molecular entity, such as a protein).

Chemical and other entity annotators 402 receive documents from large scale unstructured data sources 401 and annotate them with identifiers of chemicals and other entities. Relationship annotators 403 annotate the documents with relationships between chemicals and other entities. Natural language processing job server 404 is responsible for performing the natural language processing calculations requested by chemical and other entity annotators 402 and by relationship annotators 403 and processes the resulting annotations and the corresponding documents from the large scale unstructured data sources and stores the annotated documents in annotated data storage 405 in an appropriate data structure format such that all annotations extracted upon an individual document, or all occurrences of a particular entity annotated across a selection of documents, etc., can be readily queried.

Structured data processors 424 process data from large scale structured data sources 423. This can include parsing the schemas of these structured data sources and extracting information pertaining to the properties and attributes of each chemical compound asserted therein, and formatting that information in an appropriate data structure format such that all properties and attributes of an individual chemical compound, or all chemical compounds with selected properties and attributes within specified ranges, etc., can be readily queried. Structured data processors 424 thereafter store processed structured data in structured data storage 425.

In accordance with the illustrative embodiment, structured data in structured data storage 425 include but are not limited to structured data formats that express features or properties of a chemical. In one example embodiment, the data formats include tables and databases containing for each of a set of compounds data including but not limited to their molecular weights or the concentration of each compound necessary to inhibit the behavior of a target protein by 50% (i.e., the IC50).

Chemical information processors 414 receive information concerning chemicals and other entities and relationships from natural language processing job server 404 and receive data from structured data processor 424. Chemical information processors 414 perform calculations on the received data and store results in calculated data storage 415. Calculations performed by the chemical information processors 414 concern determinations made computationally on the basis of the received chemical compounds, and may constitute computed measurements, simulations, and alternative representations of the received chemical compounds, for instance, computed measurements of lipophilicity or hydrophobicity, simulated strength of binding to a particular protein structure complex or metabolic pathways, and three-dimensional low-energy conformers or abstracted chemical representations such as reduced graphs or pharmacophoric models.

In accordance with the illustrative embodiment, calculated data in calculated data storage 415 include but are not limited to the atomic structure of the chemical compound itself, calculated based on some input chemical name or structure definition, including both two- and three-dimensional representations (e.g., the two-dimensional chemical graph or connection table describing how the individual constituent atoms are chemically bonded) and abstractions and measured or simulated properties and attributes thereof.

The annotated data storage 405, calculated data storage 415, and structured data storage are combined into unified storage system 430. Unified storage system 430 combines structured, unstructured, and calculated data for chemicals and allow the use of the resulting combined representations of chemicals as structured, unstructured, and calculated attributes in computational predictive modeling for the real-time prediction of chemical properties. In accordance with the illustrative embodiment, the combination of large scale structured, unstructured, and calculated data in unified storage system 430 includes but is not limited to the combination of one or more sources of structured, unstructured, and calculated data in a computational model trained on the combination of the large scale data sources.

In the front end, user interface 450 receives requests for predictive analytics in real-time. In one example embodiment, user interface 450 includes Representational State Transfer (REST) service calls. The request specifies one or more chemicals for real-time predictive analytics.

In the back end, analytics jobs manager 443 receives the requests from user interface 450. Data access layer 444 accesses the combined structured, unstructured, and calculated data from unified storage system 430. Analytics jobs manager sends the request and appropriate data to analytics jobs server 442, which performs analytics techniques and predicts properties of the one or more chemicals based on real-time prediction computational model 441. In accordance with an example embodiment, computational model 441 includes but is not limited to machine learning, deep learning, neural networks, and related models, trained on the combination of large scale data sources. Computational model 441 produces in real time one or more outputs that constitute the predictions of one or more properties of the one or more chemicals. Analytics jobs manager 443 provides the one or more outputs to user interface 450.

Figure 5:
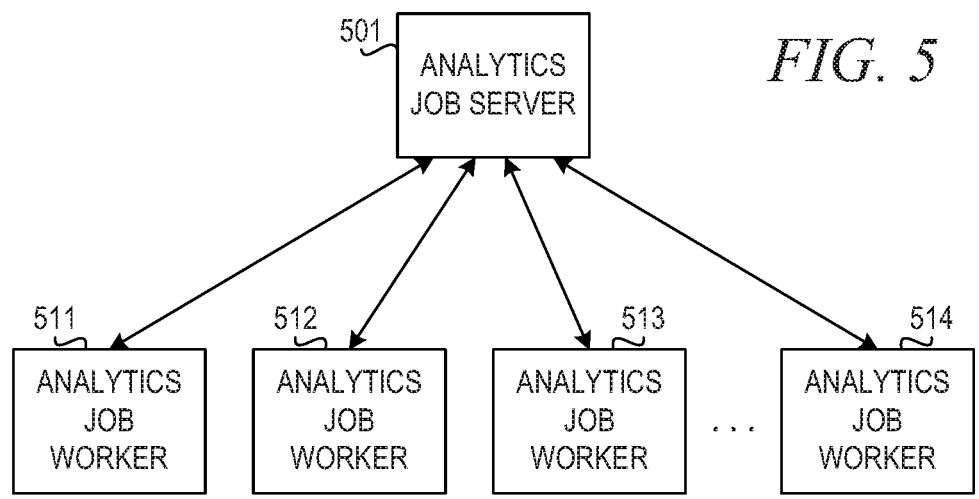
FIG. 5 is a block diagram illustrating components for extending real-time prediction for scalability in accordance with an illustrative embodiment.

FIG. 5 is a block diagram illustrating components for extending real-time prediction for scalability in accordance with an illustrative embodiment. The processing of relevant data could still be a bottleneck for real-time analytics. FIG. 5 illustrates how distributed prediction can be applied for faster runtime response. In particular, the distributed runtime can be built on top of mature frameworks like Apache Spark™ and Unstructured Information Management Architecture (UIMA) or new frameworks that can benefit from multiple workers. Analytics job server 501 sends jobs to analytics job workers 511-514. In accordance with the illustrative embodiment, the number of analytics job workers 511-514 can be extended for scalability.

Thus, the illustrative embodiment provides a software engine that takes as input data extracted from structured and unstructured data sources and produces output that is readable by a human or by software. In one embodiment, the software engine is an independent component that reads this data from other independent components that perform the processing of structured and unstructured data sources. In an alternative embodiment, the software engine is a part of a larger component that includes the processing of structured and unstructured data sources.

In one embodiment, the software engine is embodied as an independent engine. One or more components process structured data. One or more components process unstructured data. The software engine reads as input the data processed by the above components, extracts features and properties of chemicals from this data, calculates chemical structures and properties, and produces as output one or more predictions of one or more properties of one or more chemicals. An optional component interprets the output for human readability.

Figure 6:
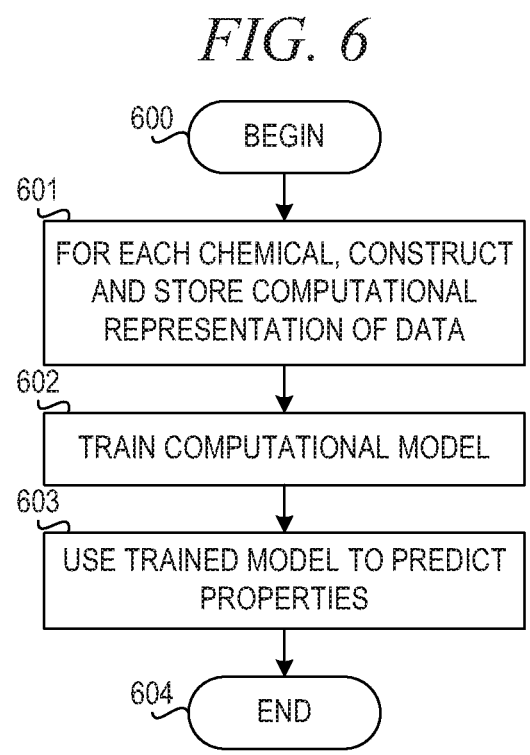
FIG. 6 is a flowchart illustrating operation of an engine for generating and storing structured, unstructured, and calculated data in a unified storage system in accordance with an illustrative embodiment.

FIG. 6 is a flowchart illustrating operation of an engine for generating and storing structured, unstructured, and calculated data in a unified storage system in accordance with an illustrative embodiment. Operation begins (block 600), and for each chemical for which data is provided as input in structured or unstructured formats, the software engine constructs and stores a computational representation of the data, comprising elements extracted from structured and unstructured sources (block 601). In one embodiment, such a representation includes but is not limited to a vector of attributes of the chemical, encoding therein the presence, absence, multiplicity or other details of a particular feature of the chemical extracted from the data. In an example embodiment, this includes but is not limited to the presence, absence, multiplicity, etc. of unstructured information such as adjacent or co-occurring words and phrases from unstructured text, adjacent or co-occurring entities from unstructured text, properties of the descriptive features of the text itself including but not limited to author and publication information, etc. In an example embodiment, this includes the presence, absence, multiplicity, etc. of structured information including but not limited to $IC_{50}$ values, boiling points, molecular mass, etc. In one example embodiment, this includes the presence, absence, multiplicity, etc. of calculated information about the chemical structure itself including but not limited to how the constituent atoms of the chemical are chemically bonded, information about the range of possible three-dimensional distances between constituent atoms of the chemical, etc.

The software engine trains a computational model (block 602). Accordingly, the extensive calculated data and data extracted from structured and unstructured data sources and represented computationally are used as input for the trained model. This includes but is not limited to model creation methodologies wherein the data is segmented into training, test, and validation sets, and iteratively trained until a particular threshold of predictive accuracy is obtained.

After training, the software engine uses the trained model to process data received as input and produces corresponding predicted properties (block 603). Thereafter, operation ends (block 604).

FIG. 7 is a flowchart illustrating operation of a software engine for large scale data analytics and real-time prediction in accordance with an illustrative embodiment. Operation begins (block 700), and a user of the software engine designs a chemical compound and enters this into the system (block 701). In one embodiment, the entered chemical compound is novel and accordingly does not occur in unstructured or structured data sources. However, data for the input chemical can be calculated based on the entered chemical itself (block 702), including but not limited to attributes related to the constituent atoms of the entered chemical and the manner in which they are chemically bonded. This example may represent, for instance, the application of the software engine to the prediction of a wide variety of properties of new chemical compounds designed by human experts or by computer software within an early-stage pharmaceutical drug discovery process, as a means of identifying potential applications of the chemical, and the automated, large scale application of this embodiment to computationally screen a very large number of potential chemical compounds to identify those most promising for experimentation or further computational study. Furthermore, although the entered chemical compound is novel and does not occur in the unstructured or structured data sources, the entire range of chemicals that do occur in unstructured and structured data sources are represented within the model trained by the software engine, and information therefrom is leveraged within the model, for instance, the unstructured and structured information concerning compounds that are chemically related to the novel input compound can be utilized to enhance predictive accuracy and present supporting evidence to a user.

In an alternative embodiment, the user selects a pre-existing chemical compound and enters this into the system. The entered chemical compound does occur in one or more unstructured or structured data sources. The computed representation of this chemical based on data extracted from unstructured and structured data sources, in addition to calculated data created based on the entered chemical itself, and/or retrieved from the storage system in block 702. In this example, the entered chemical is not novel; however, the predicted properties of the chemical are of interest for revealing potential novel applications of the chemical. This example may represent, for instance, the application of the software engine to predict previously untested properties of the chemical in order to identify possible new applications of an existing chemical, also known as "repurposing." The entire range of other chemicals that occur in the unstructured and structured data sources are represented within the model trained by the software engine, and information therefrom is leveraged within the model, for instance, the unstructured and structured information concerning compounds that are chemically related to the novel input compound can be utilized to enhance predictive accuracy and present supporting evidence to a user.

The software engine identifies similar known chemicals represented in the computational model (block 703), compares the entered chemical to identified known chemicals (block 704), and uses the computational model to predict properties of the input chemical based on the comparison (block 705). Thereafter, operation ends (block 706). The computed representation of the entered chemical can be compared to the representations of all other chemicals considered within the trained model, and predictions of properties of the entered chemical are generated.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and a memory comprising instructions which, when executed by the at least one processor, causes the at least one processor to implement a real-time prediction engine for real-time prediction of chemical properties through combining calculated, structured, and unstructured data at large scale, the method comprising:
   inputting, for each of a plurality of chemical structures, into a chemical information processor, unstructured chemical features and properties extracted, by a natural language processing job server, from one or more unstructured chemical information sources and structured chemical features and properties extracted, by a structured data processor, from structured chemical information sources;
   calculating, by the chemical information processor, for each of a plurality of chemical structures, calculated chemical structure features and properties based on the unstructured chemical features and properties, and the structured chemical features and properties;
   storing, by offline components executing within the real-time prediction engine, a computational representation for each of the plurality of chemical structures in a unified storage, wherein each computational representation maps a respective chemical structure to a vector of corresponding calculated chemical structure features and properties, corresponding unstructured chemical features and properties, and corresponding structured chemical features and properties;
   training, by the offline components using a machine learning training operation, a computational real-time predictive model based on the computational representations as inputs to the computational real-time predictive model, wherein the computational real-time predictive model is trained to predict properties based on an input chemical compound;
   receiving, by a user interface executing within the real-time prediction engine, a request specifying one or more chemical compounds;
   predicting, by an analytics jobs manager executing within the real-time prediction engine, one or more properties of the one or more chemical compounds using the computational real-time predictive model; and
   outputting, by the analytics jobs manager, the one or more properties of the one or more chemical compounds to the user interface, wherein the computational real-time predictive model comprises a machine learning model, a deep learning model, or a neural network.

2. The method of claim 1, further comprising processing, by the offline components, unstructured data describing the plurality of chemical structures to extract unstructured chemical features and properties.

3. The method of claim 2, wherein the unstructured chemical features and properties comprise generic names, systematic names, adjacent or co-occurring words or phrases, relationships between the chemical structure and words or phrases, assertion of attributes, or assertion of effects of the chemical structure.

4. The method of claim 1, further comprising processing, by the offline components, structured data describing the plurality of chemicals to extract structured chemical features and properties.

5. The method of claim 4, wherein the structured chemical features and properties comprise molecular weight or $IC_{50}$ values.

6. The method of claim 1, further comprising generating, by the offline components for each of the plurality of chemicals, chemical structure features based on the unstructured data and the structured data.

7. The method of claim 6, wherein the chemical structure features comprise an atomistic structure of the chemical structure or a two-or three-dimensional representation, or a two-dimensional chemical graph or connection table describing how individual constituent atoms of the chemical structure are chemically bonded.

8. The method of claim 1, wherein predicting the one or more properties of the one or more chemical compounds comprises sending by an analytics job server a plurality of real-time predictive analytics jobs to a plurality of analytics job worker components.

9. The method of claim 1, wherein predicting the one or more properties of the one or more chemical compounds comprises:
   identifying chemical structures similar to the one or more chemical compounds;

comparing the one or more chemical compounds to the identified similar chemical structures; and using the computational real-time predictive model to predict the one or more properties of the one or more chemical compounds based on results of the comparison.

10. A computer program product comprising a non-transitory computer readable medium having a computer readable program stored therein, wherein the computer readable program, when executed on a computing device, causes the computing device to implement a real-time prediction engine for real-time prediction of chemical properties through combining calculated, structured, and unstructured data at large scale, wherein the computer readable program causes the computing device to:

input, for each of a plurality of chemical structures, into a chemical information processor, unstructured chemical features and properties extracted, by a natural language processing job server, from one or more unstructured chemical information sources and structured chemical features and properties extracted, by a structured data processor, from structured chemical information sources;

calculate, by the chemical information processor, for each of a plurality of chemical structures, calculated chemical structure features and properties based on the unstructured chemical features and properties, and the structured chemical features and properties;

store, by offline components executing within the real-time prediction engine, a computational representation for each of the plurality of chemical structures in a unified storage, wherein each computational representation maps a respective chemical structure to a vector of corresponding calculated chemical structure features and properties, corresponding unstructured chemical features and properties, and corresponding structured chemical features and properties;

train, by the offline components using a machine learning training operation, a computational real-time predictive model based on the computational representations as inputs to the computational real-time predictive model, wherein the computational real-time predictive model is trained to predict properties based on an input chemical compound;

receive, by a user interface executing within the real-time prediction engine, a request specifying one or more chemical compounds;

predict, by an analytics jobs manager executing within the real-time prediction engine, one or more properties of the one or more chemical compounds using the computational real-time predictive model; and output, by the analytics jobs manager, the one or more properties of the one or more chemical compounds to the user interface, wherein the computational real-time predictive model comprises a machine learning model, a deep learning model, or a neural network.

11. The computer program product of claim 10, wherein the computer readable program causes the computing device to process, by the offline components, unstructured data describing the plurality of chemical structures to extract unstructured chemical features and properties.

12. The computer program product of claim 11, wherein the unstructured chemical features and properties comprise generic names, systematic names, adjacent or co-occurring words or phrases, relationships between the chemical structure and words or phrases, assertion of attributes, or assertion of effects of the chemical structure.

13. The computer program product of claim 10, wherein the computer readable program causes the computing device to process, by the offline components, structured data describing the plurality of chemicals to extract structured chemical features and properties.

14. The computer program product of claim 13, wherein the structured chemical features and properties comprise molecular weight or $IC_{50}$ values.

15. The computer program product of claim 10, wherein the computer readable program causes the computing device to generate, by the offline components for each of the plurality of chemicals, chemical structure features based on the unstructured data and the structured data.

16. The computer program product of claim 15, wherein the chemical structure features comprise an atomistic structure of the chemical structure or a two-or three-dimensional representation, or a two-dimensional chemical graph or connection table describing how individual constituent atoms of the chemical structure are chemically bonded.

17. The computer program product of claim 10, wherein predicting the one or more properties of the one or more chemical compounds comprises sending by an analytics job server a plurality of real-time predictive analytics jobs to a plurality of analytics job worker components.

18. An apparatus comprising:

a processor; and a memory coupled to the processor, wherein the memory comprises instructions which, when executed by the processor, cause the processor to implement a real-time prediction engine for real-time prediction of chemical properties through combining calculated, structured, and unstructured data at large scale, wherein the instructions cause the processor to:

input, for each of a plurality of chemical structures, into a chemical information processor, unstructured chemical features and properties extracted, by a natural language processing job server, from one or more unstructured chemical information sources and structured chemical features and properties extracted, by a structured data processor, from structured chemical information sources;

calculate, by the chemical information processor, for each of a plurality of chemical structures, calculated chemical structure features and properties based on the unstructured chemical features and properties, and the structured chemical features and properties;

store, by offline components executing within the real-time prediction engine, a computational representation for each of the plurality of chemical structures in a unified storage, wherein each computational representation maps a respective chemical structure to a vector of corresponding calculated chemical structure features and properties, corresponding unstructured chemical features and properties, and corresponding structured chemical features and properties;

train, by the offline components using a machine learning training operation, a computational real-time predictive model based on the computational representations as inputs to the computational real-time predictive model, wherein the computational real-time predictive model is trained to predict properties based on an input chemical compound;

receive, by a user interface executing within the real-time prediction engine, a request specifying one or more chemical compounds;

predict, by an analytics jobs manager executing within the real-time prediction engine, one or more properties of the one or more chemical compounds using the computational real-time predictive model; and output, by the analytics jobs manager, the one or more properties of the one or more chemical compounds to the user interface, wherein the computational real-time predictive model comprises a machine learning model, a deep learning model, or a neural network.

19. The method of claim 1, wherein the calculated chemical structure features and properties comprises at least one of chemical functional groups, individual smallest ring systems, and fused ring systems.

20. The method of claim 1, wherein the calculated chemical structure features and properties comprise an atomic structure specified as a three-dimensional representation in a connection table that describes how individual constituent atoms are chemically bonded, and simulated properties and attributes of the atomic structure.

* * * * *